(12) United States Patent
Tada et al.

(10) Patent No.: US 12,714,379 B2
(45) Date of Patent: Aug. 25, 2026

(54) MEDICAL SYSTEM

(71) Applicant: TERUMO KABUSHIKI KAISHA, Tokyo (JP)

(72) Inventors: Yuichi Tada, Santa Clara, CA (US); Yoichiro Kuwano, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 626 days.

(21) Appl. No.: 18/169,836

(22) Filed: Feb. 15, 2023

(65) Prior Publication Data

US 2023/0277144 A1 Sep. 7, 2023

(30) Foreign Application Priority Data

Mar. 4, 2022 (JP) ................................ 2022-033301

(51) Int. Cl.

*A61B 6/12* (2006.01)
*A61B 90/00* (2016.01)

(52) U.S. Cl.

CPC .......... *A61B 6/12* (2013.01); *A61B 2090/364* (2016.02)

(58) Field of Classification Search

CPC ...... A61B 17/320725; A61B 17/32075; A61B 17/320783; A61B 17/320758; A61B 17/3203; A61B 2017/320032; A61B 17/320092; A61B 2017/32113; A61B 2017/32091; A61B 17/3211; A61B 17/32113; A61B 6/12; A61B 2090/364; A61B 90/37; A61B 2090/376; A61B 2090/3937; A61B 2090/3966

See application file for complete search history.

(56) References Cited

U.S. PATENT DOCUMENTS

2012/0330336 A1* 12/2012 Simpson ........ A61B 17/320783 606/159
2015/0105791 A1* 4/2015 Truckai ............ A61B 17/00234 606/115
2015/0265807 A1* 9/2015 Park .................. A61M 25/0133 901/2
2017/0065288 A1* 3/2017 Imai ............... A61B 17/320725
2017/0333052 A1* 11/2017 Ding ................ A61B 17/00234

(Continued)

FOREIGN PATENT DOCUMENTS

EP 1566150 B1 * 8/2005 ........... A01K 63/003
JP 2021-053062 A 4/2021

*Primary Examiner* — Pascal M Bui Pho
*Assistant Examiner* — Michael Yiming Fang
(74) *Attorney, Agent, or Firm* — Kim & Stewart LLP

(57) ABSTRACT

A medical system includes a device including a drive shaft, a cutter for cutting an object within a cutting range, a tube surrounding the shaft and including a contrast marker, and rollers for rotating and moving the pipe, a memory storing information including cross-sectional images of the cavity, an imaging device capturing images of the marker, and a controller determining, based on the information, a target position of the cutter and a target orientation of the marker in an image to be captured when the object is within the range, determining a current position of the cutter based on a captured image and moving the pipe such that the cutter reaches the target position, and determining an orientation of the marker in a captured image and rotating the pipe such that the marker in the image has the target orientation.

20 Claims, 6 Drawing Sheets

(56) References Cited

U.S. PATENT DOCUMENTS

| | | | | |
|---|---|---|---|---|
| 2020/0060718 | A1* | 2/2020 | Patel | A61B 5/6852 |
| 2021/0209757 | A1* | 7/2021 | Min | A61K 49/04 |
| 2021/0220623 | A1* | 7/2021 | Humbert | A61B 17/11 |

* cited by examiner 10
20
21
23
24
25
26
27
28
30
31
40
41
50
70
80
90
100
101
102
110
112
113
130

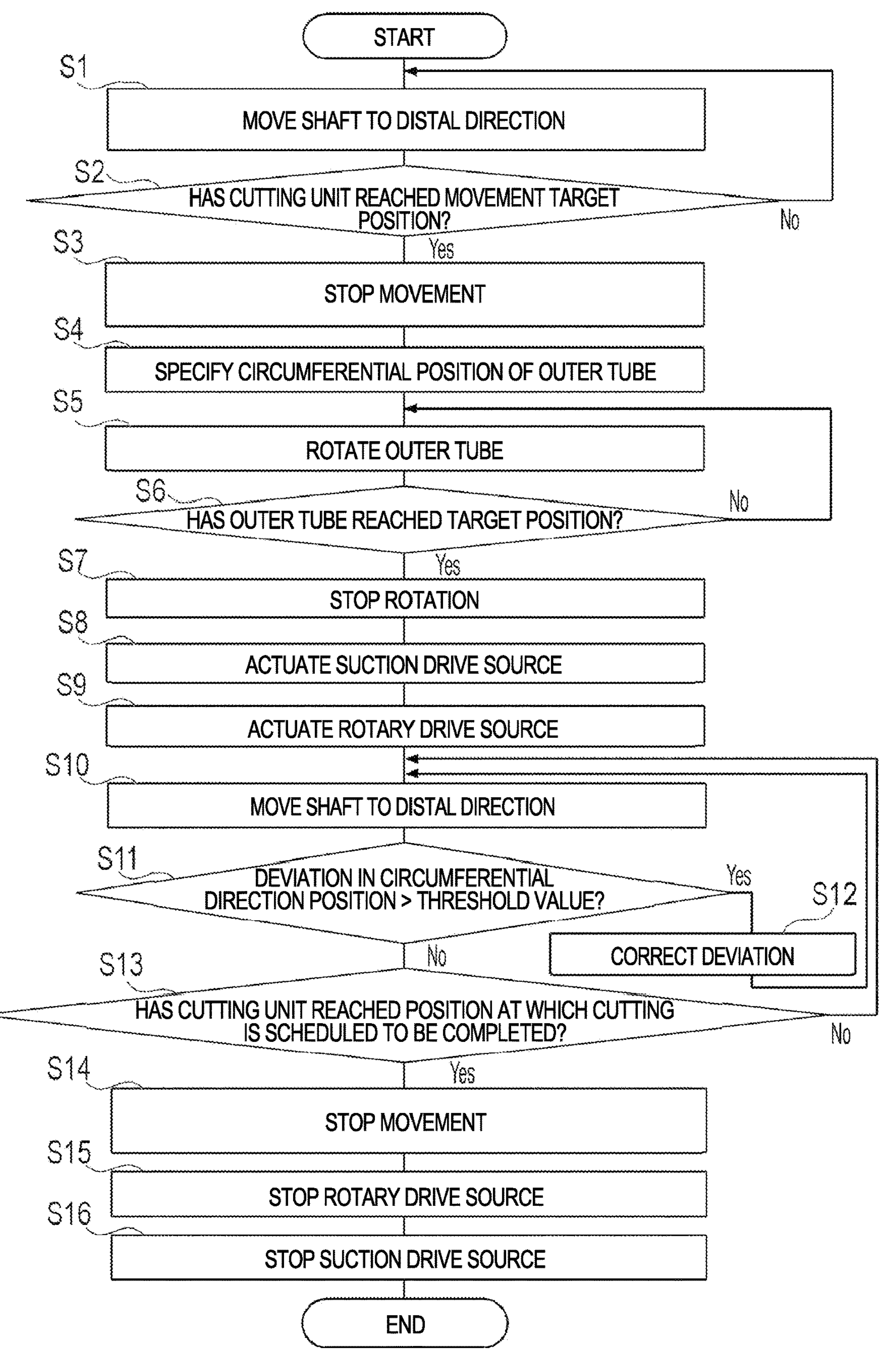
FIG. 4
START
S1
MOVE SHAFT TO DISTAL DIRECTION
S2
HAS CUTTING UNIT REACHED MOVEMENT TARGET POSITION?
No
Yes
S3
STOP MOVEMENT
S4
SPECIFY CIRCUMFERENTIAL POSITION OF OUTER TUBE
S5
ROTATE OUTER TUBE
S6
HAS OUTER TUBE REACHED TARGET POSITION?
No
Yes
S7
STOP ROTATION
S8
ACTUATE SUCTION DRIVE SOURCE
S9
ACTUATE ROTARY DRIVE SOURCE
S10
MOVE SHAFT TO DISTAL DIRECTION
S11
DEVIATION IN CIRCUMFERENTIAL DIRECTION POSITION > THRESHOLD VALUE?
Yes
S12
CORRECT DEVIATION
No
S13
HAS CUTTING UNIT REACHED POSITION AT WHICH CUTTING IS SCHEDULED TO BE COMPLETED?
No
Yes
S14
STOP MOVEMENT
S15
STOP ROTARY DRIVE SOURCE
S16
STOP SUCTION DRIVE SOURCE
END

S
α
R
A
30
P
B
26
β

X
R
C
28
T

FIG. 7A
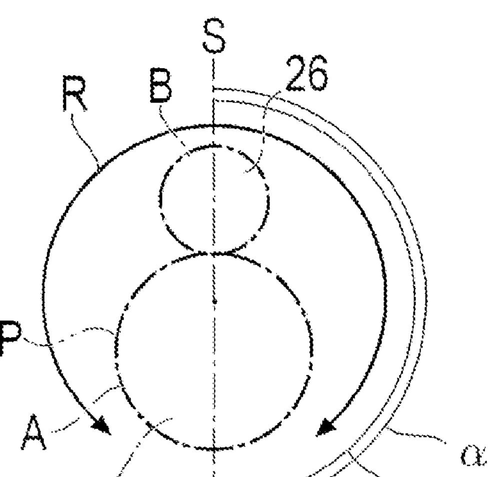
FIG. 7B
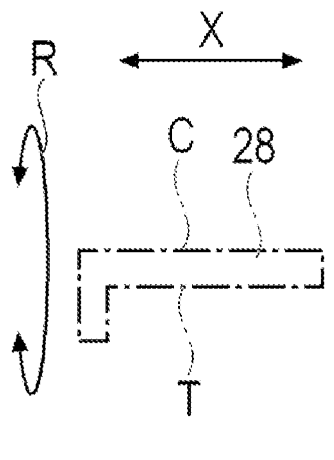
FIG. 8
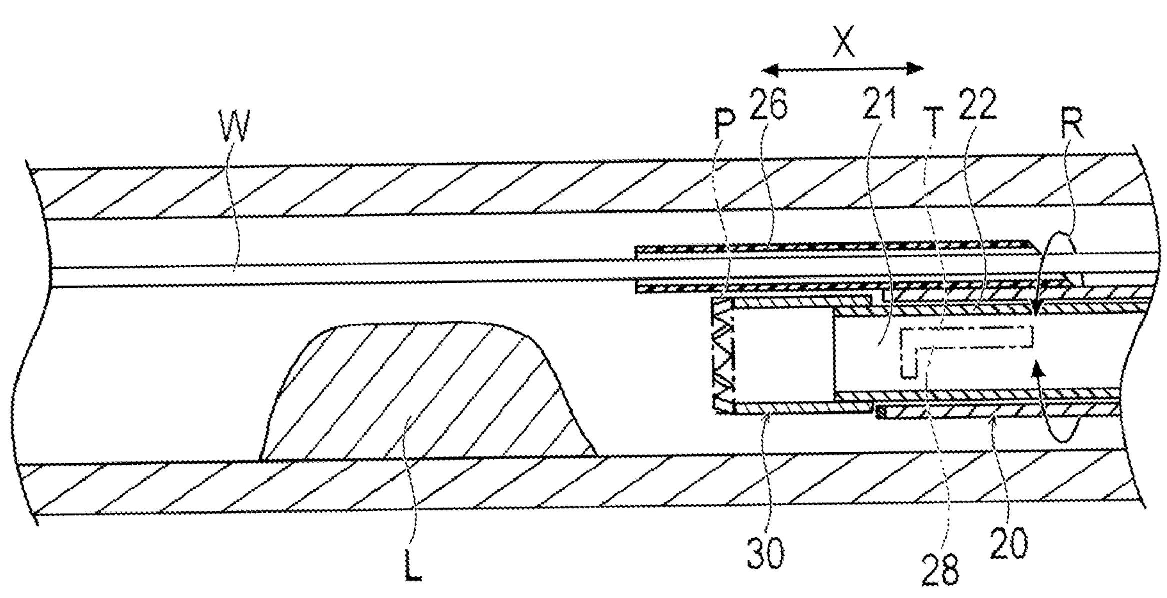

MEDICAL SYSTEM

CROSS-REFERENCE TO RELATED APPLICATION(S)

This application is based on and claims the benefit of priority from Japanese patent application No. 2022-033301, filed Mar. 4, 2022, the entire contents of which are incorporated herein by reference.

BACKGROUND

Technical Field

Embodiments described herein relate generally to a medical system for removing an object in a biological body cavity.

Related Art

In recent years, a medical device that removes an object such as a thrombus, a plaque, or the like from a biological body cavity such as a blood vessel to the outside of the body has been used. For example, an atherectomy device is used to cut and remove an affected area including a plaque or thrombus in a blood vessel.

SUMMARY

Affected areas including a plaque and a thrombus in a blood vessel are often unevenly distributed in the blood vessel. In order to bring a cutting unit of an atherectomy device or the like into contact with an unevenly distributed affected area, it is necessary to orient the cutting unit in the blood vessel properly with reference to the X-ray images captured during the operation. However, since an X-ray image often used in a medical procedure is typically a two-dimensional image, it is necessary to align the unevenly distributed affected area and the cutting unit by acquiring multiple images while rotating the X-ray imaging device, and this is complicated.

For example, there is a conventional catheter in which the shape of a contrast marker is set such that the appearance of the contrast marker observed by an X-ray imaging device varies depending on the circumferential position of the catheter. However, even if the circumferential position of the catheter can be specified by the X-ray imaging device, it is necessary for the operator to adjust the catheter to have a target rotation angle.

A medical system includes a device for removing an object in a body cavity, the device including a rotatable drive shaft, a cutter attached to a distal end of the drive shaft and by which the object within a cutting range is cut, an outer tube surrounding the drive shaft and on which a contrast marker is formed, and one or more rollers configured to rotate the outer tube to adjust the cutting range of the cutter, and move the outer tube along a rotation axis thereof. The medical system further includes a memory that stores body cavity information including cross-sectional images of the body cavity including the object, an imaging device configured to capture one or more images of the contrast marker in the body cavity, and a controller. The controller is configured to: based on the body cavity information, determine a target position of the cutter in the body cavity for removing the object and a target orientation of the contrast marker in an image to be captured by the imaging device when the object is within the cutting range, determine a current position of the cutter in the body cavity based on a first image captured by the imaging device, and control the rollers to move the outer tube such that the cutter reaches the target position, and determine an orientation of the contrast marker in a second image captured by the imaging device, and control the rollers to rotate the outer tube such that the contrast marker in the second image has the target orientation.

The medical system configured as described above is capable of automatically rotating the outer tube of the drive shaft inserted into a body cavity such as a blood vessel and adjusting the cutting range of the cutter attached to the distal end of the drive shaft, thereby making control of the cutter in the body cavity easy and improving operability.

BRIEF DESCRIPTION OF DRAWINGS

FIG. 4 is a flowchart showing an operation of the medical system.

FIG. 7A is a view showing a cutting range of the cutting unit that has reached the target position.

FIG. 7B is a view showing the target shape of the contrast marker.

FIG. 8 is a cross-sectional view showing the cutting range of the cutting unit at the target position.

DETAILED DESCRIPTION

Figure 1:
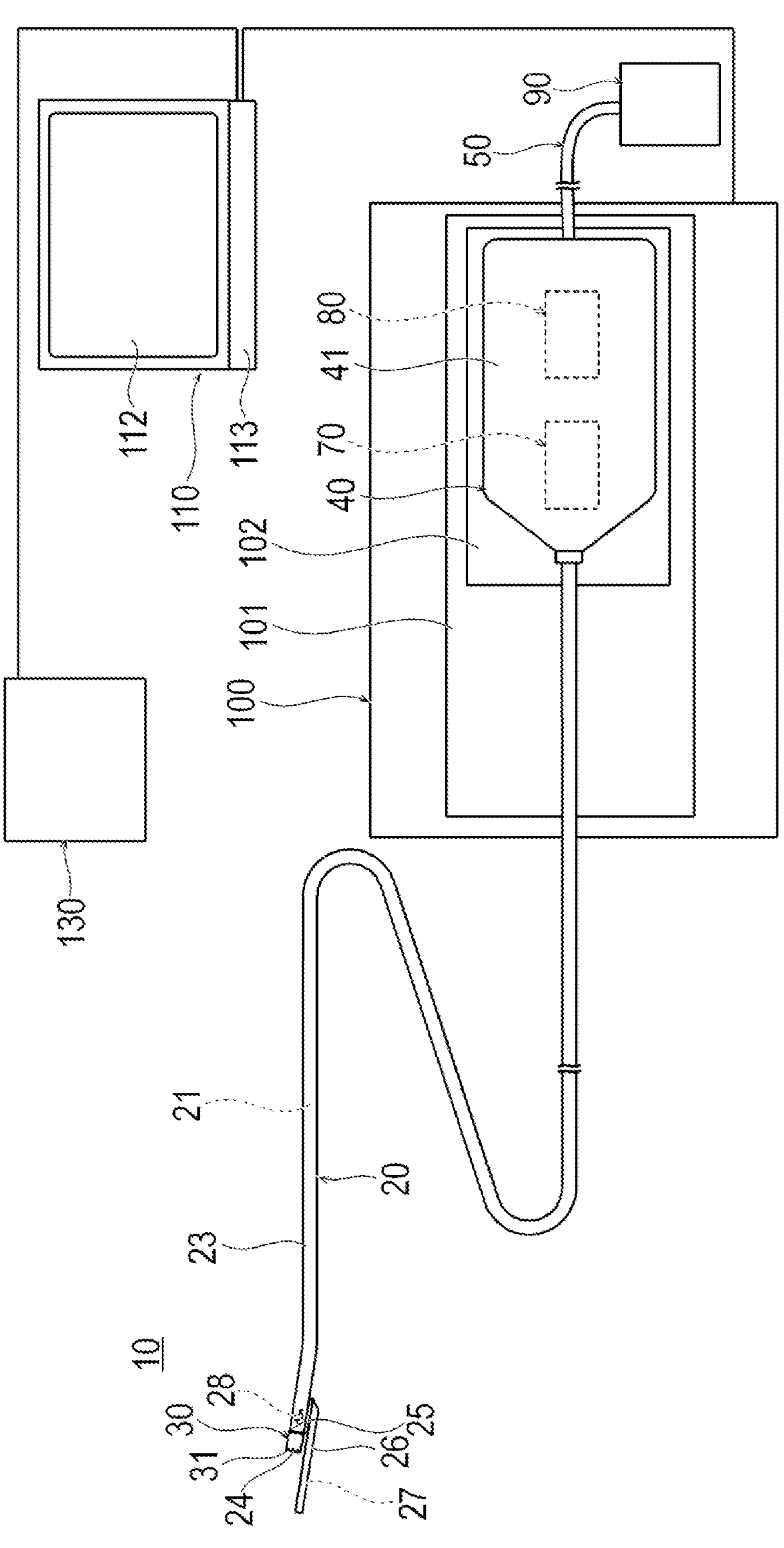
FIG. 1 is a schematic view of a medical system according to an embodiment.

Embodiments of the present invention will be described below with reference to the drawings. The size and ratio of each element in the drawings may be exaggerated for convenience of description and may be different from the actual size and ratio.

A medical system 1 according to an embodiment is inserted into a blood vessel in acute lower limb ischemia or deep-vein thrombosis, and used for a treatment including cutting and removing an object such as a thrombus, a plaque, an atheroma, and a calcified area. In the present description, a side of a device to be inserted into a blood vessel is referred to as “distal side”, and a side to be operated by an operator is referred to as “proximal side”. The object to be cut and removed is not necessarily limited to a thrombus, a plaque, an atheroma, and a calcified area, and any object that can exist in a biological body cavity can be cut and removed by the medical system 1.

Figure 2:
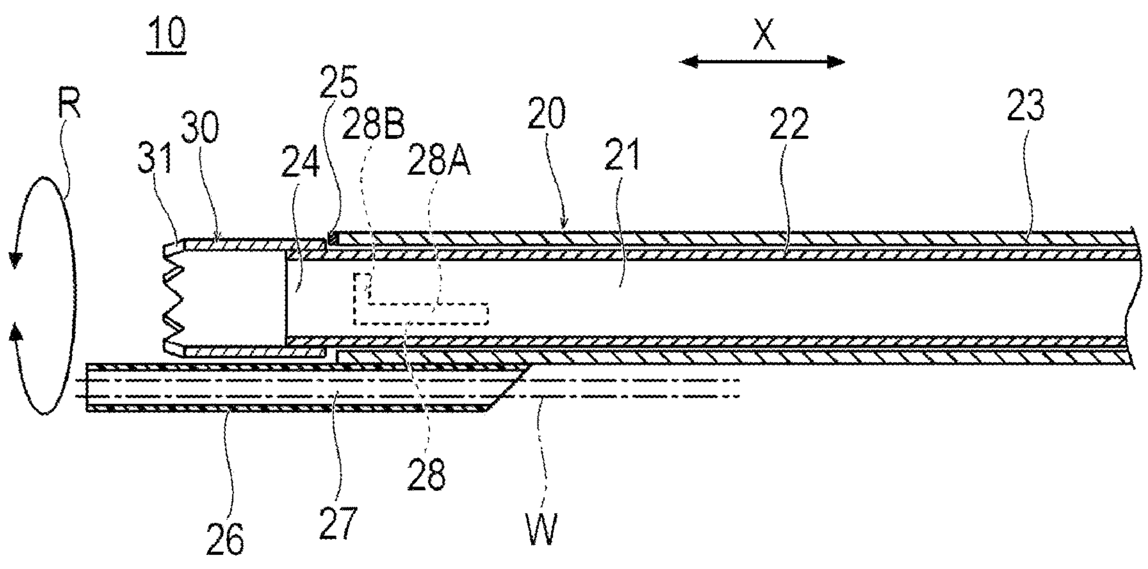
FIG. 2 is an enlarged cross-sectional view of a distal portion of a medical device in the medical system.
Figure 3:
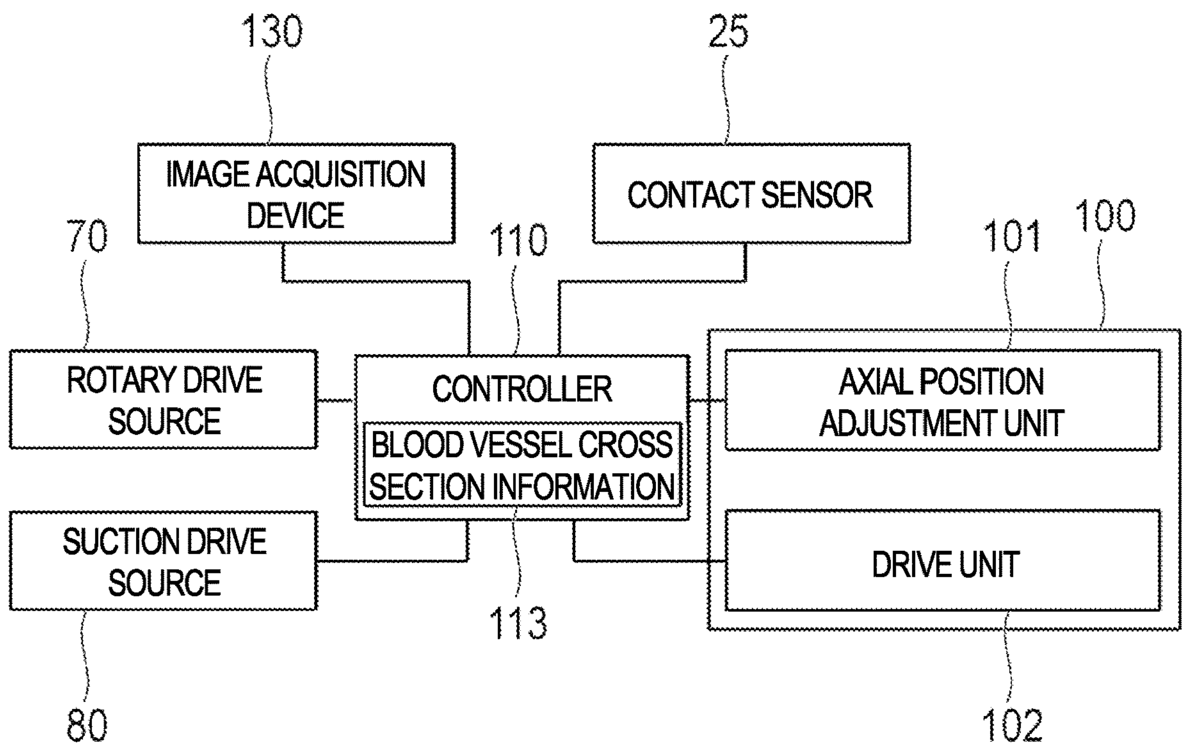
FIG. 3 is a hardware block diagram of the medical system.

As shown in FIGS. 1 to 3, the medical system 1 includes a medical device 10 in which a cutting unit 30 configured to cut an object is arranged at its distal portion, a position adjustment unit 100 configured to adjust a position of the medical device 10, and a controller 110 configured to control the operation of the medical device 10 and the position adjustment unit 100.

The medical device 10 includes an elongated shaft portion 20 including a discharge lumen 21 through which an object can pass to the proximal side, the cutting unit 30 arranged at a distal portion of the shaft portion 20, and an operation portion 40 to which a proximal portion of the shaft portion 20 is coupled. The medical device 10 further includes a rotary drive source 70 configured to rotate a drive shaft 22 provided in the shaft portion 20, a suction drive source 80 communicating with the discharge lumen 21 provided in the shaft portion 20, a discharge path 50 through which a waste liquid sucked by the suction drive source 80 is discharged, and a waste liquid bag 90 communicating with the discharge path 50 and configured to receive the waste liquid through the discharge path 50.

The shaft portion 20 includes the drive shaft 22 rotationally driven by the rotary drive source 70, an outer tube 23 configured to rotatably house the drive shaft 22, and a tip tube 26 fixed to a side surface of a distal portion of the outer tube 23.

The drive shaft 22 is coupled to the cutting unit 30 and transmits the rotational force to the cutting unit 30. The drive shaft 22 is flexible and has a characteristic capable of transmitting, to the distal side, rotational power applied from the proximal side. The drive shaft 22 is formed with the discharge lumen 21 for moving a cut object to the proximal side. The drive shaft 22 penetrates the outer tube 23, and the cutting unit 30 is fixed to the distal portion thereof. The proximal portion of the drive shaft 22 is coupled to the rotary drive source 70. The drive shaft 22 has, at the distal portion, a tip opening 24 where the discharge lumen 21 opens. The tip opening 24 is an inlet through which debris that is a suction target formed by cutting enters. The proximal portion of the drive shaft 22 is coupled to the suction drive source 80 configured to apply a suction force to the discharge lumen 21. The discharge lumen 21 may be formed not inside the drive shaft 22 but between the outer tube 23 and the drive shaft 22 or inside another tube provided inside the drive shaft 22. The drive shaft 22 may be an optical fiber that transfers light energy.

The cutting unit 30 is a cutter configured to cut, into a small size, an object such as a thrombus, a plaque, or a calcified area. Therefore, "cut" means applying a force to a contacted object to reduce the size thereof. The application method of force in cutting and the shape and form of the object after cutting are not limited. The cutting unit 30 has enough strength to cut the above-described object. The cutting unit 30 is fixed to the distal portion of the drive shaft 22. The cutting unit 30 is a cylinder protruding toward the distal side of the drive shaft 22. The cutting unit 30 may be hollow and in communication with the discharge lumen 21. The distal end of the cutting unit 30 includes a sharp blade 31. The shape of the blade 31 is not particularly limited. The cutting unit 30 may have a large number of fine abrasive grains in place of a blade. The cutting unit 30 may be the distal end of an optical fiber that can reduce the size of the object described above.

The rotary drive source 70 is arranged inside the operation portion 40 to rotate the drive shaft 22. The rotary drive source 70 is, for example, a motor. The rotational speed of the rotary drive source 70 is not particularly limited, and is, for example, 5,000 rpm to 200,000 rpm.

The suction drive source 80 is arranged inside the operation portion 40. The suction drive source 80 is, for example, a pump, and in communication with the proximal end of the discharge lumen 21 of the drive shaft 22 to apply a suction force (i.e., a negative pressure) to the discharge lumen 21. The suction drive source 80 moves the waste liquid sucked through the discharge lumen 21 to the downstream side, and discharges the waste liquid to the waste liquid bag 90. The suction drive source 80 is, for example, a peristaltic pump, but may be a diaphragm pump. The peristaltic pump partially crushes a tube by a plurality of rollers, and moves the crushed position, thereby moving the fluid inside the tube.

The outer tube 23 is a tubular body having flexibility, and has its proximal portion fixed to the operation portion 40. The distal portion of the outer tube 23 is positioned on the distal side of the cutting unit 30. On the outer surface of the distal portion of the outer tube 23, which is a part of the shaft portion 20, an L-shaped contrast marker 28 is formed. The location of the contrast marker 28 is indicated in FIG. 2 by dashed lines. The contrast marker 28 includes a first portion 28A extending along an axial direction X of the shaft portion 20 and a second portion 28B extending from the distal end of the first portion 28A to one side in a circumferential direction R. Thus, when viewed from the axial direction of the shaft portion 20, the second portion 28B has an arc shape extending along the curved outer surface of the outer tube 23. The contrast marker 28 is made of a radiopaque material. Examples of radiopaque material include two or more alloys including gold, platinum, silver, bismuth, and tungsten. A shape C of the contrast marker 28 in a two-dimensional image captured by an image acquisition device 130, which is an external X-ray imaging device, is uniquely determined corresponding to the position or the angle of the outer tube 23 or the shaft portion 20 in the circumferential direction R centered on the axial center of the outer tube 23 or the shaft portion 20. The position of the outer tube 23 or the shaft portion 20) in the circumferential direction R indicates an angle formed by a specific portion of the outer tube 23 or the shaft portion 20 around the axial center of the shaft portion 20 with respect to a preset reference position S. That is, when the outer tube 23 rotates with respect to the blood vessel and the angle of the outer tube 23 in the circumferential direction R changes, the angle of the contrast marker 28 in the outer tube 23 changes in the circumferential direction R, and accordingly, the shape C of the contrast marker 28 in the two-dimensional image captured by the X-ray imaging device changes. This makes it possible to inversely calculate the angle of the outer tube 23 in the circumferential direction R from the shape C of the contrast marker 28 in the two-dimensional image. Therefore, the controller 110 can determine the angle of the outer tube 23 in the circumferential direction R by performing calculation on the basis of image information including the contrast marker 28 obtained from the X-ray imaging device. The shape C of the contrast marker 28 is not particularly limited as long as the angle in the circumferential direction R of the outer tube 23 can be calculated, and may be, for example, a circular tube shape in which a plurality of holes arranged in a spiral shape are formed. The outer tube 23 may have a curved portion that bends at a predetermined angle at its distal portion. Due to this, by rotating the outer tube 23, it is possible to change its position on the distal side relative to the curved portion of the outer tube 23 and make the cutting unit 30 easily come into contact with the object to be removed.

Figures 5, 6A, 6B:
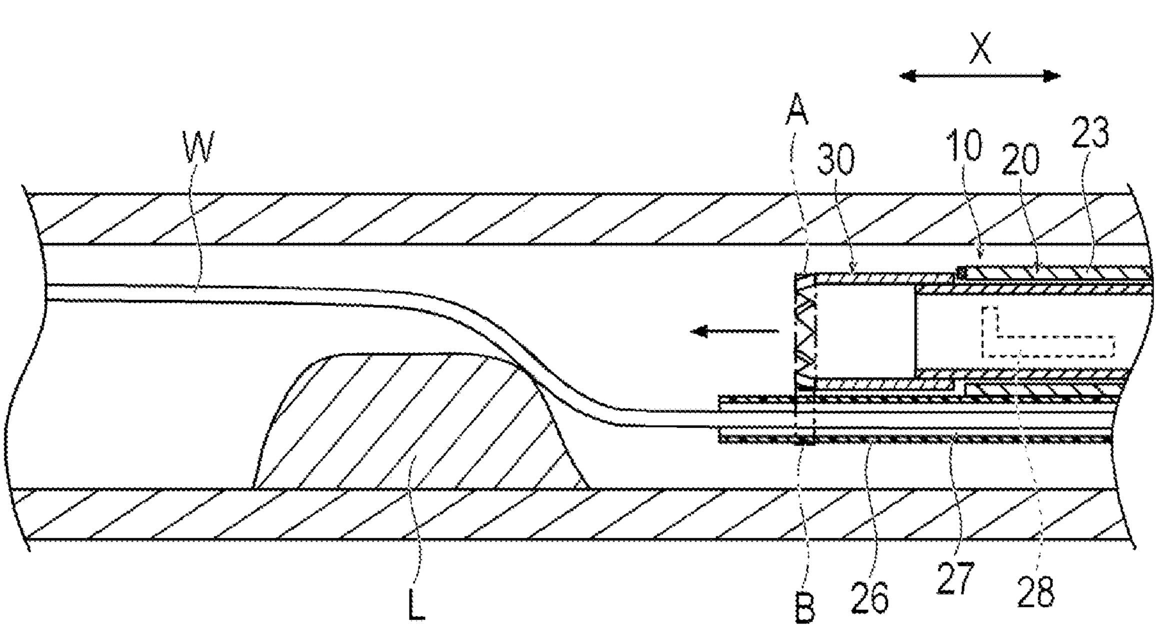
FIG. 5 is a cross-sectional view of the cutting unit of the medical device near an affected area.
FIG. 6A is a view showing a cutting range of the cutting unit at present and target positions.
FIG. 6B is a view showing present and target shapes of a contrast marker.

The tip tube 26 is a tubular body having flexibility, and is fixed to the outer peripheral surface of the distal portion of the outer tube 23. The tip tube 26 has a guide wire lumen 27 into which a guide wire W can be inserted. When the outer tube 23 rotates, the angle of the tip tube 26 in the circumferential direction R with respect to the outer tube 23 changes. At the distal portion of the shaft portion 20, the tip tube 26, which is a non-cutting unit not having cutting ability, and the cutting unit 30, which can exhibit the cutting ability only within a limited range by arranging the tip tube 26, are arranged in the circumferential direction R of the shaft portion 20. Therefore, when the shaft portion 20 rotates, as shown in FIGS. 6A and 6B, a non-cutting range B of the tip tube 26, which is a non-cutting unit, rotates, and a cutting range A of the cutting unit 30 can move in the circumferential direction R.

At the distal end of the outer tube 23, a contact sensor 25 is disposed as shown in FIGS. 1 to 3. When the cutting unit 30 located on the distal side comes into contact with a hard object such as an affected area, the contact sensor 25 can detect stress by coming into contact with the cutting unit 30 and transmit a detection result to the controller 110 described later. The position of the contact sensor 25 is not limited to the distal end of the outer tube 23, and may be arranged in the cutting unit 30, for example.

The discharge path 50 is arranged between the suction drive source 80 and the waste liquid bag 90, and conveys, to the waste liquid bag 90, the waste liquid discharged from the suction drive source 80. The discharge path 50 is preferably transparent or translucent so that the operator can view the flow of the waste liquid.

The position adjustment unit 100 includes an axial position adjustment unit 101 configured to move the shaft portion 20 along the axial direction X, and a drive unit 102 configured to rotate the shaft portion 20 in the circumferential direction R about the axial direction X.

The axial position adjustment unit 101 is coupled to the operation portion 40 and/or the shaft portion 20 of the medical device 10, and includes a linear motion drive mechanism having one or more rollers rotated by a motor and configured to linearly move the operation portion 40 and/or the shaft portion 20 along the axial direction X. The drive of the linear motion drive mechanism is controlled by the controller 110. This enables the axial position adjustment unit 101 to move the shaft portion 20 and the cutting unit 30 along the axial direction X.

The drive unit 102 is coupled to the operation portion 40 and/or the shaft portion 20 of the medical device 10, and includes a rotary drive mechanism having one or more rollers rotated by a motor and configured to rotate the operation portion 40 and/or the shaft portion 20 about the axial direction X. The drive of the rotary drive mechanism is controlled by the controller 110. This enables the drive unit 102 to rotate the shaft portion 20 about the axial direction X. The position adjustment unit 100, which includes the axial position adjustment unit 101 and the drive unit 102, may be a three-dimensionally operable robot arm or the like.

The controller 110 includes a memory and an arithmetic circuit. The memory stores programs and various parameters. The arithmetic circuit is, for example, a processor such as a central processing unit (CPU), and can load and execute the programs and various parameters stored in the memory.

The controller 110 further includes a display unit 111 such as a monitor configured to display information as an image and an input unit 112 such as a touchscreen, a keyboard, and/or a mouse so that the operator can perform operations and various settings.

The controller 110 stores blood vessel cross section information 113 of a patient before performing a treatment by the medical system 1. The blood vessel cross section information 113 is, for example, a three-dimensional blood vessel image acquired by an ultrasonic image diagnostic device, a computed tomography (CT) device, a magnetic resonance imaging (MRI) device, or the like. On the basis of the information received from the image acquisition device 130 and the contact sensor 25 and the blood vessel cross section information 113 that is stored, the controller 110 controls the operations of the rotary drive source 70, the suction drive source 80, the axial position adjustment unit 101, and the drive unit 102.

The controller 110 can be connected to the image acquisition device 130 to receive image information, and can receive a detection result from the contact sensor 25. The image acquisition device 130 is an X-ray imaging device with which the medical device 10 inserted into a blood vessel can be observed from outside the body. In the present embodiment, the image acquisition device 130 is a detection unit configured to detect the angle of the cutting range A of the cutting unit 30 in the circumferential direction R of the shaft portion 20. The X-ray imaging device can acquire a two-dimensional image. The controller 110 can superimpose the two-dimensional image acquired by the image acquisition device 130 on the blood vessel cross section information 113 that is stored. The image acquisition device 130 is not limited to the X-ray imaging device as long as an image can be acquired in a state where the medical device 10 is inserted into a blood vessel, and may be, for example, an ultrasonic image diagnosis device, a CT device, or the like. Therefore, the image to be obtained may be not a two-dimensional image but a three-dimensional image. When the obtained image is a three-dimensional image, the shape C of the contrast marker 28 needs not to be a shape with which the angle of the outer tube 23 in the circumferential direction R can be determined from the two-dimensional image.

On the basis of the information received from the image acquisition device 130 and the contact sensor 25 and the blood vessel cross section information 113 that is stored, the controller 110 controls the operations of the rotary drive source 70, the suction drive source 80, the axial position adjustment unit 101, and the drive unit 102.

Next, operation control of the medical system 1 will be described with reference to the flowchart shown in FIG. 4.

Before performing a treatment by the medical system 1, the controller 110 aligns, in the axial direction X and the circumferential direction R, the position of an affected area in a body cavity shown in the two-dimensional image captured by the X-ray imaging device on the blood vessel cross section information 113 (e.g., a three-dimensional blood vessel image) so that the pixel coordinates of those images are associated with each other. With this alignment, the controller 110 can specify the position of the affected area position of the blood vessel cross section information 113 in the two-dimensional image captured by the X-ray imaging device. After performing the alignment, the controller 110 sets the reference position S (for example, 12 o'clock in the blood vessel cross section information 113) and calculates an angle β in the circumferential direction R from the reference position S to the affected area position as shown in FIGS. 6A and 6B. The controller 110 sets in advance the shape C of the contrast marker 28 in the two-dimensional image captured by the X-ray imaging device corresponding to an angle α in the circumferential direction R from the reference position S to the cutting range A of the cutting unit 30. For example, the direction and degree of protrusion of the second portion 28B with respect to the first portion 28A of the contrast marker 28 in the two-dimensional image corresponding to the angle α in the circumferential direction R of the cutting range A of the cutting unit 30 are set in advance. The controller 110 stores the blood vessel cross section information 113 of the patient. The operator specifies the position of an affected area L of the blood vessel from the blood vessel cross section information 113 displayed on the display unit 111 or the like. The position of the affected area L means a position in the blood vessel extending direction in the blood vessel to be treated, a position (i.e., angle in the circumferential direction of the blood vessel, and the like. Subsequently, the operator decides a target position P in the circumferential direction R of the cutting range A with respect to the blood vessel and a movement target position in the axial direction X of the cutting unit 30 with respect to the blood vessel for arranging the cutting unit 30 at a desired position for cutting the affected area L having been specified, and sets the target positions in the controller 110 using the input unit 112. The target position P in the circumferential direction R and the movement target position in the axial direction X may be calculated by the controller 110.

Next, the operator inserts the proximal portion of the guide wire W into the guide wire lumen 27 of the medical device 10. Thereafter, the operator inserts the medical device 10 into the blood vessel along the guide wire W. Next, the operator operates the medical system 1 to start control by the controller 110.

The controller 110 actuates the axial position adjustment unit 101 to move the shaft portion 20 in the distal direction as shown in FIG. 5 (S1). On the basis of the information from the image acquisition device 130, the controller 110 specifies the position of the contrast marker 28 in the axial direction X with respect to the blood vessel, and moves the shaft portion 20 in the distal direction until the cutting unit 30 reaches the movement target position.

Upon determining that the cutting unit 30 has reached the movement target position (S2), the controller 110 controls the axial position adjustment unit 101 to stop the movement of the shaft portion 20 in the distal direction (S3). Next, the controller 110 specifies the angle α in the circumferential direction R of the cutting range A with respect to the blood vessel as shown in FIGS. 6A and 6B and FIGS. 7A and 7B from the shape C of the contrast marker 28 included in the image information obtained from the image acquisition device 130 (S4).

Next, the controller 110 actuates the drive unit 102 to rotate the outer tube 23 (S5). While controlling the drive unit 101 to rotate the outer tube 23, the controller 110 calculates the angle α in the circumferential direction R of the cutting range A at present of the cutting unit 30 from the shape C of the contrast marker 28 in the two-dimensional image captured by the X-ray imaging device. Then, the controller 110 controls the drive unit 102 to rotate the shaft portion 20 until the angle α in the circumferential direction R of the cutting range A specified by the shape C of the contrast marker 28 in the two-dimensional image captured by the X-ray imaging device coincides with the calculated angle β in the circumferential direction R from the reference position S to the affected area position. That is, by rotating the outer tube 23 by the angle obtained by subtracting the angle α in the circumferential direction R of the cutting range A at present from the angle β in the circumferential direction R from the reference position S to the affected area position, the cutting range A coincides with the target position P. Alternatively, from the image information captured by the image acquisition device 130, the controller 110 may determine the target position P in the cutting range A and a target shape T of the contrast marker shape 28 in the captured image when the cutting range A reaches the target position P, and control the rotation of the drive unit 101 until the image acquisition device 130 detects the target shape T of the contrast marker shape 28 in the captured image at the target position P. The controller 110 sequentially calculates the angle α of the contrast marker 28 in the circumferential direction R on the basis of the information from the image acquisition device 130, and rotates the outer tube 23 until the cutting range A reaches the target position P as shown in FIGS. 7A, 7B, and 8. Upon determining that the angle α in the circumferential direction R of the cutting range A has reached the angle β of the affected area position that is the target position P (S6), the controller 110 controls the drive unit 102 to stop the rotation of the outer tube 23 (S7). That is, after the angle α in the circumferential direction R of the cutting range A of the cutting unit 30 coincides with the angle β in the circumferential direction R from the reference position S to the affected area position, the controller 110 controls the drive unit 102 to stop the rotation of the outer tube 23. Due to this, the shaft portion 20 including the tip tube 26 and the cutting unit 30 can reach the desired position for cutting the affected area L in the circumferential direction R in the blood vessel. As an example, in a case where the affected area L is only on a portion of the inner wall surface of the blood vessel, the controller 110 moves the tip tube 26, which is the non-cutting range B, to the side on which the affected area L is not present, and moves the cutting unit 30, which is the cutting range A, to the side on which the affected area L is present. Since the cutting range A has a range in the circumferential direction R, the angle α can be, for example, a median value thereof. Since the target position P has a range in the circumferential direction R, the angle β can be, for example, a median value thereof.

Figure 9:
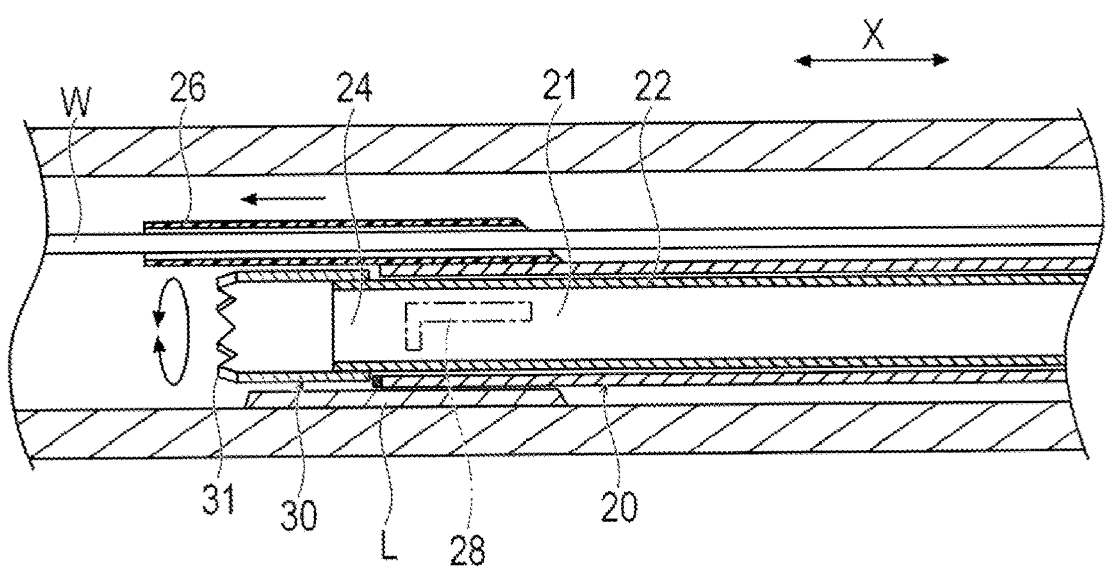
FIG. 9 is a cross-sectional view showing an affected area being cut by the cutting unit.

Next, the controller 110 actuates the suction drive source 80 (S8). Due to this, a suction force is applied on the discharge lumen 21. Subsequently, the controller 110 actuates the rotary drive source 70 to rotate the drive shaft 22 and the cutting unit 30 (S9). Next, the controller 110 actuates the axial position adjustment unit 101 to move the shaft portion 20 in the distal direction as shown in FIG. 9 (S10). The controller 110 moves the shaft portion 20 and the cutting unit 30 in the distal direction until the position of the cutting unit 30 in the axial direction X with respect to the blood vessel, which can be determined using the information from the image acquisition device 130, reaches the position at which the cutting of the affected area L is scheduled to be completed. The position of the cutting unit 30 at which the cutting of the affected area L is scheduled to be completed is calculated by the controller 110 from the blood vessel cross section information 113.

When the cutting unit 30 moves in the distal direction, the blade 31 of the cutting unit 30 comes into contact with the affected area L and cuts the affected area L. The affected area L cut by the cutting unit 30 becomes debris and is sucked into the discharge lumen 21 from the tip opening 24 of the drive shaft 22. The waste liquid containing the sucked debris is discharged from the discharge flow path to the waste liquid bag 90 through the suction drive source 80.

After actuating the rotary drive source 70, the controller 110 calculates a deviation (i.e., the angle β−α) of the angle α of the cutting range A in the circumferential direction R from the target position P on the basis of the information from the image acquisition device 130. Then, in a case where the calculated deviation exceeds a preset threshold value (S11), the controller 110 actuates the drive unit 102 to control the angle α in the circumferential direction R of the cutting range A to coincide with the target position P (S12). That is, the controller 110 performs control so that the angle α in the circumferential direction R of the cutting range A does not deviate from the angle β of the target position P as much as possible. Due to this, the angle α in the circumferential direction R of the cutting range A that receives the force by cutting the affected area L is suppressed from deviating from the angle β, of the target position P, and the affected area L can be appropriately cut. The angle β, of the target position P in the circumferential direction R may change depending on the position in the extending direction of the blood vessel. In this case, by optimally changing the angle α of the cutting range A in the circumferential direction R according to the position in the extending direction of the blood vessel, the controller 110 can effectively cut the affected area L.

Upon determining that the position of the cutting unit 30 in the axial direction X with respect to the blood vessel, obtained from the information from the image acquisition device 130, has reached the position at which the cutting is scheduled to be completed (S13), the controller 110 controls the axial position adjustment unit 101 to stop the movement of the shaft portion 20 in the distal direction (S14). This allows the cutting of the affected area L to be stopped at an appropriate position of the blood vessel, and the safety to be improved. The controller 110 may control the axial position adjustment unit 101 so that the cutting unit 30 cuts the affected area while reciprocating along the axial direction X in the blood vessel.

Next, the controller 110 controls the rotary drive source 70 to stop the rotation of the cutting unit 30 (S15). Subsequently, the controller 110 controls the suction drive source 80 to stop suction (S16). Due to this, the operation control of the medical system 1 by the controller 110 is completed.

As described above, the medical system 1 according to the present embodiment includes: the elongated shaft portion 20; the cutting unit 30 at a distal portion of the shaft portion 20 and having the cutting range A limited in a circumferential direction of the shaft portion 20; the tip tube 26 in the shaft portion 20 outside the cutting range A of the cutting unit 30; the drive unit 102 configured to rotate the shaft portion 20 for changing the angle α of the cutting range A of the cutting unit 30 with respect to the body cavity; the controller 110 configured to control an operation of the drive unit 102; and the image acquisition device 130 configured to capture an image of the contrast marker 28 on the shaft portion 20 to detect a shape thereof in the captured image. The controller 110 calculates, from the blood vessel cross section information 113 having been input, the target position P of the cutting range A that covers an affected area, and the shape C of the contrast marker 28 in the captured image at the target position P, and controls rotation of the drive unit 102 until the image acquisition device 130 detects the target shape T of the contrast marker 28 at the target position P in the captured image. Due to this, the medical system 1 is capable of automatically rotating and adjusting the cutting range A of the cutting unit 30 at the distal end of the shaft portion 20 to the desired target position P for cutting, thereby making control of a position in the circumferential direction R of the shaft portion 20 easy, and improving operability.

The controller 110 can specify the angle α of the cutting range A of the cutting unit 30 from the shape C of the contrast marker 28 in the image acquired from the image acquisition device 130. This allows the controller 110 to perform control of moving the cutting range A of the cutting unit 30 to a desired position (for example, target position P).

The shaft portion 20 includes the radiopaque contrast marker 28, the two-dimensional shape C of the contrast marker 28 observed from a predetermined position uniquely corresponds to the angle α of the cutting range A of the cutting unit 30 in the circumferential direction R of the shaft portion 20, and the controller 110 calculates a position of the contrast marker 28 of the shaft portion 20 from a two-dimensional image input from the image acquisition device 130 (for example, an X-ray imaging device). This allows the medical system 1 to automatically detect the angle α of the cutting range A of the cutting unit 30 in the circumferential direction R of the shaft portion 20, and therefore the angle of the shaft portion 20 is easily controlled and operability is improved.

The medical system 1 includes the drive shaft 22 inside the shaft portion 20 and having a distal portion to which the cutting unit 30 is fixed, and the rotary drive source 70 configured to rotate the drive shaft 22, and the controller 110 actuates the rotary drive source 70 when the angle α of the cutting range A of the cutting unit 30 reaches the target position P. This allows the medical system 1 to automatically start cutting by the cutting unit 30.

The medical system 1 includes the suction drive source 80 configured to apply a suction force to the discharge lumen 21 inside the shaft portion 20, and the controller 110 actuates the suction drive source 80 when the angle α of the cutting range A of the cutting unit 30 reaches the target position P. This allows the medical system 1 to automatically determine and perform start of suction, and thus operability is improved.

The medical system 1 includes the drive shaft 22 inside the shaft portion 20 and having the distal portion to which the cutting unit 30 is fixed, and the rotary drive source 70 configured to rotate the drive shaft 22, and the controller 110 actuates the suction drive source 80 before actuating the rotary drive source 70. This allows the medical system 1 to automatically determine and perform start of cutting, and thus operability is improved. Since the medical system 1 starts suction before starting to cut, it is possible to effectively suppress debris generated by cutting from scattering inside the body without being sucked.

The medical system 1 includes the axial position adjustment unit 101 configured to move the shaft portion 20 or the cutting unit 30 along the axial direction X of the shaft portion 20, and the controller 110 calculates the movement target position of the shaft portion 20 or the cutting unit 30 from the blood vessel cross section information 113 and the position in the axial direction X of the shaft portion 20 or the cutting unit 30, and controls the axial position adjustment unit 101 in such a manner that the shaft portion 20 or the cutting unit 30 reach the movement target position. This allows the medical system 1 to automatically arrange the cutting unit 30 to the movement target position in the axial direction X desirable for cutting in addition to the target position P in the circumferential direction R, and therefore the position of the cutting range A of the cutting unit 30 can be controlled more automatically, and the operability is improved.

When the angle α of the cutting range A of the cutting unit 30 in the circumferential direction R of the shaft portion 20 deviates from the target position P during cutting by the cutting unit 30, the controller 110 controls the axial position adjustment unit 101 to move the cutting unit 30 toward the proximal direction. Due to this, when the cutting unit 30 receives a force during cutting and deviates from the target position P in the circumferential direction R, by moving the cutting unit 30 toward the proximal direction, readjustment can be performed so that the cutting unit 30 reaches a desired position, and cutting can be continued.

When the angle α of the cutting range A of the cutting unit 30 in the circumferential direction R of the shaft portion 20 deviates from the target position P during cutting by the cutting unit 30, the controller 110 controls the drive unit 102 to perform adjustment to reduce the deviation. This makes it possible to suppress the cutting unit 30 from deviating from the target position P by receiving a force during cutting and to maintain the position of the cutting unit 30 at a position desirable for cutting, and therefore it is possible to suppress deterioration of cutting performance.

The present invention is not limited to the above-described embodiment, and various modifications can be made by those skilled in the art within the technical idea of the present invention. For example, the cutting unit 30 does not need to be a rotating body, and may be, for example, a structure configured to perform cutting by moving along the axial direction X or a member configured to emit a laser beam. When the cutting unit 30 is not a rotating body, the contrast marker 28 may be arranged not in the shaft portion 20 but in the cutting unit 30.

As a modification of the control described above, when the cutting unit 30 before starting cutting comes into contact with the affected area L, the controller 110 may actuate the rotary drive source 70 to start cutting of the affected area L by the cutting unit 30. That is, the controller 110 actuates the suction drive source 80 to start suction (S8), and thereafter, does not actuate the axial position adjustment unit 101 but actuates the rotary drive source 70 to move the shaft portion 20 and the cutting unit 30 toward the distal direction. When the cutting unit 30 comes into contact with the affected area L, the cutting unit 30 is pushed toward the proximal side of the affected area L, and the contact sensor 25 detects stress (see FIGS. 2 and 3). When the detection result by the contact sensor 25 exceeds a preset threshold value, the controller 110 can determine that the cutting unit 30 has come into contact with the affected area L and actuate the rotary drive source 70. Due to this, the cutting unit 30 rotates together with the drive shaft 22, and the affected area L is cut. The contact sensor 25 may be arranged in the cutting unit 30. When the detection result by the contact sensor 25 exceeds a preset threshold value, the controller 110 may determine that the cutting unit 30 has come into contact with the affected area L and actuate both the suction drive source 80 and the rotary drive source 70. Therefore, the medical system 1 according to the modification includes the contact sensor 25 in the cutting unit 30 or the shaft portion 20 and configured to detect stress applied to the cutting unit 30, and the controller 110 receives a detection result of the contact sensor 25, and controls actuation of the suction drive source 80 and/or the rotary drive source 70 on the basis of the detection result. This allows the medical system 1 to automatically determine that the cutting unit 30 has come into contact with the affected area L on the basis of the detection result from the contact sensor 25 and can automatically perform actuation of suction and/or cutting, and therefore the operability is improved.

Figure 10:
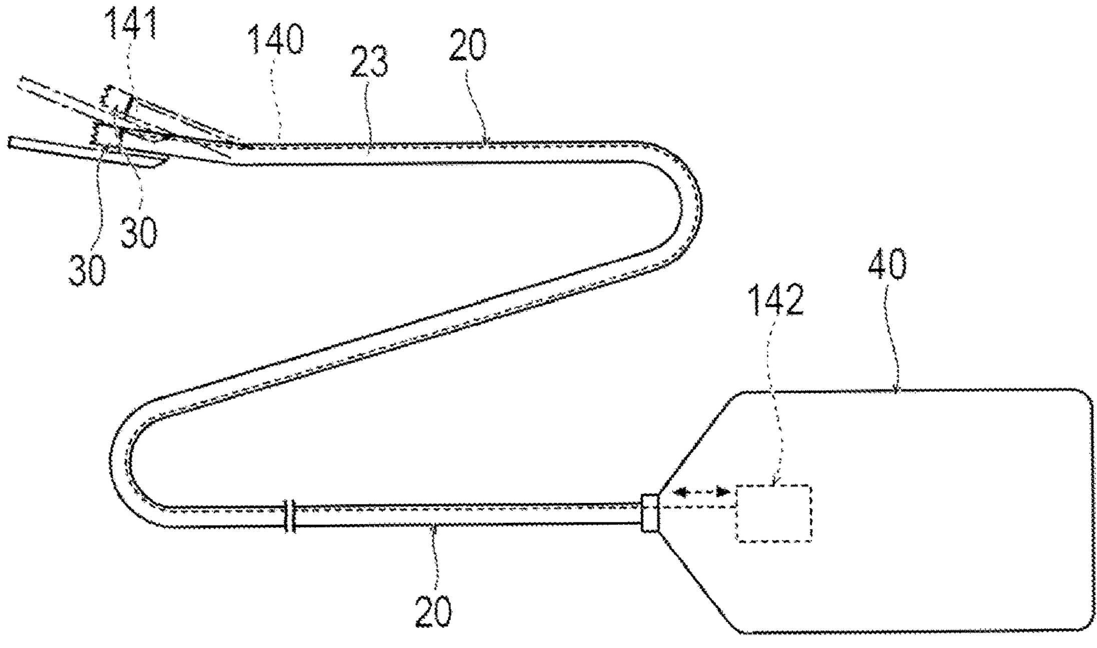
FIG. 10 is a schematic view showing a modification of the medical system.

As in the modification shown in FIG. 10, the medical system 1 may include a structure for automatically performing an operation of bending the distal portion of the shaft portion 20. For example, a traction wire 140 is disposed inside the outer tube 23 of the medical device 10, and a tip 141 of the traction wire 140 is fixed at a specific position in the circumferential direction on the inner peripheral surface of the outer tube 23. A proximal portion of the traction wire 140 is coupled to a curve drive source 142 arranged inside the operation portion 40. The operation of the curve drive source 142 is controlled by the controller 110, and the curve drive source 142 can move the traction wire 140 toward the distal direction and the proximal direction. Therefore, the controller 110 can control the curve drive source 142 to pull the traction wire 140 in the proximal direction and bend the distal portion of the shaft portion 20 in one direction. Therefore, the controller 110 can control the curve drive source 142 to pull the traction wire 140 in the proximal direction and return the distal portion of the shaft portion 20 to the original shape by the elastic force of the shaft portion 20. As described above, the medical system 1 includes the curve drive source 142 configured to curve the shaft portion 20 in such a manner that the axial center of the shaft portion 20 is bent, and the controller 110 can calculate a target angle of a curve angle of the shaft portion 20 from the blood vessel cross section information 113 and the angle α of the cutting range A of the cutting unit 30 in the circumferential direction R of the shaft portion 20, and control the curve drive source 142 in such a manner that the curve of the shaft portion 20 has the target angle. The angle α of the cutting range A of the cutting unit 30 can be measured using the image captured by the image acquisition device 130. This allows the medical system 1 to automatically move the cutting unit 30 to a position desired for cutting by curving the shaft portion 20. This allows the medical system 1 to control, with high accuracy, the position of the cutting unit 30 in the blood vessel to a desired position, and therefore the cutting performance can be improved.

The controller 110 may align a side branch branching from a blood vessel shown in the blood vessel cross section information 113 prepared in advance (e.g., a three-dimensional image) and the side branch shown in an image captured by the image acquisition device 130 during operation. This allows the medical system 1 to align, with high accuracy, the blood vessel cross section information 113 and the image captured by the image acquisition device 130, and can improve the accuracy of the control of the medical system 1 by the controller 110.

In addition, by determining the initial angle of the cutting range A of the cutting unit 30, and then detecting, by the drive unit 102, for example, the angle by which the cutting unit 30 has rotated during operation, the medical system 1 can specify the angle α of the cutting range A of the cutting unit 30 without observing the contrast marker 28 by the image acquisition device 130.

What is claimed is:

1. A medical system comprising:
- a device for removing an object in a body cavity, the device including:
  - a rotatable drive shaft,
  - a cutter attached to a distal end of the drive shaft and by which the object within a cutting range is cut,
  - an outer tube surrounding the drive shaft and on which a contrast marker is formed, the contrast marker including:
    - a first portion extending along a rotation axis of the outer tube, and
    - a second portion connected to one end of the first portion and extending along a circumferential direction of the outer tube, and
  - one or more rollers configured to rotate the outer tube to adjust the cutting range of the cutter, and move the outer tube along the rotation axis thereof;
- a memory that stores body cavity information including cross-sectional images of the body cavity including the object;
- an imaging device configured to capture one or more images of the contrast marker in the body cavity; and
- a controller configured to:
  - based on the body cavity information, determine a target position of the cutter in the body cavity for removing the object and a target shape of the contrast marker in an image to be captured by the imaging device when the object is within the cutting range, determine a current position of the cutter in the body cavity based on a first image captured by the imaging device, and control the rollers to move the outer tube such that the cutter reaches the target position, and determine a shape of the contrast marker in a second image captured by the imaging device, and control the rollers to rotate the outer tube such that the shape of the contrast marker in the second image matches the target shape.

2. The medical system according to claim 1, wherein the controller is further configured to calculate an angle for the outer tube to be rotated when the cutter is at the target position based on the shape of the contrast marker in the second image and the target shape of the contrast marker.

3. The medical system according to claim 1, wherein the contrast marker is a radiopaque contrast marker, and the first portion is longer than the second portion.

4. The medical system according to claim 3, wherein the images captured by the imaging device are two-dimensional images of the body cavity, and the controller is configured to determine the cutting range of the cutter in the body cavity based on a two-dimensional shape of the contrast marker in a captured image.

5. The medical system according to claim 3, wherein the imaging device is an X-ray imaging device.

6. The medical system according to claim 1, further comprising:

a motor configured to rotate the drive shaft, wherein the controller is further configured to:

determine whether the cutter has reached the target position based on an image captured by the imaging device, and upon determining that the cutter has reached the target position, control the motor to rotate the drive shaft.

7. The medical system according to claim 1, further comprising:

a pump configured to apply a suction force to a discharge lumen inside the drive shaft and through which the object that has been cut is discharged, wherein the controller is further configured to:

determine whether the cutter has reached the target position based on an image captured by the imaging device, and upon determining that the cutter has reached the target position, control the pump to apply the suction force to the discharge lumen.

8. The medical system according to claim 7, further comprising:

a motor configured to rotate the drive shaft, wherein upon determining that the cutter has reached the target position, the controller controls the pump to apply the suction force to the discharge lumen after controlling the motor to rotate the drive shaft.

9. The medical system according to claim 1, further comprising:

a pump configured to apply a suction force to a discharge lumen inside the drive shaft and through which the object that has been cut is discharged;

a motor configured to rotate the drive shaft; and a contact sensor attached to the cutter or the drive shaft and configured to output a signal in response to a contact with the object, wherein the controller is further configured to control the pump to apply the suction force to the discharge lumen and/or the motor to rotate the drive shaft upon receipt of the signal from the contact sensor.

10. The medical system according to claim 1, further comprising:

a traction wire, one end of which is connected to a distal portion of the outer tube; and a curve drive source connected to the other end of the traction wire and configured to pull the traction wire such that the distal portion of the outer tube is curved, wherein the controller is further configured to:

calculate a target degree of a curve of the distal portion of the outer tube based on a shape of the contrast marker in an image captured by the imaging device and the target shape of the contrast marker, and control the curve drive source to pull the traction wire such that the distal portion of the outer tube is curved by the target degree of the curve thereof.

11. The medical system according to claim 1, wherein the controller is further configured to:

determine whether the cutting range of the cutter that is rotating at the target position deviates from the target range based on a shape of the contrast marker in an image captured by the imaging device and the target shape of the contrast marker, and upon determining that the cutting range of the cutter that is rotating at the target position deviates from the target range, control the rollers to rotate the outer tube such that the shape of the contrast marker in the captured image matches the target shape thereof.

12. The medical system according to claim 11, wherein the controller is further configured to, after determining that the cutting range of the cutter that is rotating at the target position deviates from the target range, control the rollers to move the outer tube away from the object before rotating the outer tube.

13. The medical system according to claim 1, wherein the body cavity information includes a three-dimensional image of the body cavity including the object, and the controller is further configured to map an image captured by the imaging device onto the three-dimensional image using a branch of the body cavity to determine a location of the object to be removed in the captured image.

14. A method carried out by a medical system that includes:

a device for removing an object in a body cavity, the device including a rotatable drive shaft, a cutter attached to a distal end of the drive shaft and by which the object within a cutting range is cut, an outer tube surrounding the drive shaft and on which a contrast marker is formed, the contrast marker including:

a first portion extending along a rotation axis of the outer tube, and a second portion connected to one end of the first portion and extending along a circumferential direction of the outer tube, and one or more rollers configured to rotate the outer tube to adjust the cutting range of the cutter, and move the outer tube along the rotation axis thereof, the method comprising:

storing body cavity information including cross-sectional images of the body cavity including the object;

based on the body cavity information, determining a target position of the cutter in the body cavity for removing the object and a target shape of the contrast marker in an image to be captured by an imaging device when the object is within the cutting range;

capturing a first image of the contrast marker in the body cavity by the imaging device;

determining a current position of the cutter in the body cavity based on the first image, and controlling the rollers to move the outer tube such that the cutter reaches the target position;

capturing a second image of the contrast marker in the body cavity by the imaging device; and determining a shape of the contrast marker in the second image, and controlling the rollers to rotate the outer tube such that the shape of the contrast marker in the second image matches the target shape.

15. The method according to claim 14, further comprising:

calculating an angle for the outer tube to be rotated when the cutter is at the target position based on the shape of the contrast marker in the second image and the target shape of the contrast marker.

16. The method according to claim 14, wherein the contrast marker is a radiopaque contrast marker, and the first portion is longer than the second portion.

17. The method according to claim 16, wherein each of the first and second images is a two-dimensional image, and the method further comprises:

determining the cutting range of the cutter in the body cavity based on a two-dimensional shape of the contrast marker in the second image.

18. The method according to claim 14, wherein the medical system further includes a motor configured to rotate the drive shaft, and the method further comprises:

capturing a third image of the contrast marker in the body cavity;

determining whether the cutter has reached the target position based on the third image; and upon determining that the cutter has reached the target position, controlling the motor to rotate the drive shaft.

19. The method according to claim 14, wherein the medical system further includes a pump configured to apply a suction force to a discharge lumen inside the drive shaft and through which the object that has been cut is discharged, and the method further comprises:

capturing a third image of the contrast marker in the body cavity, determining whether the cutter has reached the target position based on the third image, and upon determining that the cutter has reached the target position, controlling the pump to apply the suction force to the discharge lumen.

20. A medical system comprising:

a device for removing an object in a body cavity, the device including:

a rotatable drive shaft, a cutting unit attached to a distal end of the drive shaft and by which the object within a cutting range is cut, and an outer tube surrounding the drive shaft and on which a contrast marker is formed, the contrast marker including:

a first portion extending along a rotation axis of the outer tube, and a second portion connected to one end of the first portion and extending along a circumferential direction of the outer tube;

a drive unit configured to rotate the outer tube to adjust the cutting range, and move the outer tube along the rotation axis thereof;

a memory that stores body cavity information including cross-sectional images of the body cavity including the object;

a detection unit configured to capture one or more images of the contrast marker in the body cavity; and a control unit configured to:

based on the body cavity information, determine a target position of the cutting unit in the body cavity for removing the object and a target shape of the contrast marker in an image to be captured by the detection unit when the object is within the cutting range, determine a current position of the cutting unit in the body cavity based on a first image captured by the detection unit, and control the drive unit to move the outer tube such that the cutting unit reaches the target position, and determine a shape of the contrast marker in a second image captured by the detection unit, and control the drive unit to rotate the outer tube such that the shape of the contrast marker in the second image matches the target shape.

* * * * *